(12) United States Patent
Wittenbecher et al.

(10) Patent No.: US 7,777,059 B2
(45) Date of Patent: Aug. 17, 2010

(54) COPPER(I) FORMATE COMPLEXES

(75) Inventors: Lars Wittenbecher, Mannheim (DE); Heinrich Lang, Chemnitz (DE); Yingzhong Shen, Nanjing (CN)

(73) Assignee: BASF SE, Ludwigshafen (DE)

( * ) Notice: Subject to any disclaimer, the term of this patent is extended or adjusted under 35 U.S.C. 154(b) by 1097 days.

(21) Appl. No.: 10/583,103

(22) PCT Filed: Dec. 15, 2004

(86) PCT No.: PCT/EP2004/014275

§ 371 (c)(1), (2), (4) Date: Jun. 16, 2006

(87) PCT Pub. No.: WO2005/058789

PCT Pub. Date: Jun. 30, 2005

(65) Prior Publication Data

US 2007/0197810 A1 Aug. 23, 2007

(51) Int. Cl.
C07F 1/08 (2006.01)
(52) U.S. Cl. .................... 556/112; 427/227
(58) Field of Classification Search ............... 556/112
See application file for complete search history.

(56) References Cited

U.S. PATENT DOCUMENTS 5,141,602 A 8/1992 Chen et al.
6,770,122 B2 * 8/2004 Thompson ............... 106/1.18

FOREIGN PATENT DOCUMENTS

| CN | 12 40 689 | 1/2000 |
|---|---|---|
| DE | 39 22 233 | 1/1991 |
| DE | 41 38 722 | 5/1993 |
| DE | 103 25 243 | 12/2004 |
| EP | 0 368 231 | 5/1990 |
| EP | 0 976 847 | 2/2000 |
| EP | 1 077 084 | 2/2001 |
| JP | 06/184 749 | 7/1994 |
| JP | 11/193 461 | 7/1999 |
| WO | WO-01/13426 | 2/2001 |
| WO | WO 01/94291 | 12/2001 |
| WO | WO-03 053895 | 7/2003 |

OTHER PUBLICATIONS

Bianchini et al., "Reactivity of Copper(I) Tetrahydroborates towards CO2 and COS. Structure of (triphos)Cu(n1-O2CH)," Inorg. Chem., 24, 924-931, 1985.*

Bowmaker et al., "Crystal Structures and vibrational and solid-state (CPMAS) NMR spectroscopic studies in the tris(triphenylphosphine)-copper(I) and -silver(I) formate systems," J. Chem. Soc., Dalton Trans., pp. 753-761, 2000.*
T.T. Kodas et al., The Chemistry of Metal CVD, 1994, p. 239-302.
D.K. Sohn et al., Ahn in Electrochem. Soc. 144 (1977), 3592-3596.
F.A. Cotton et al., Inorg. Chem. 39 (2000), 6072-6079.
E. Iljina et al., Mater. Sci. Eng. B18 (1993) 234-236.
S.A. Krupoder et al., J. Fluorine Chem. 73 (1995) 13-15.
M.E. Gross, J. Electrochem. Soc. 138 (8) (1991) 2422-2426.
K. Kohler et al., Organometallics 22 (2003) 4426-4432.
J.K. Kim et al., J. Korean Phys. Soc. 35 (5) (1999) 426-430.
M.J. Mouche et al., Adv. Sci. Technol. (Adv. Inorg. Films and Coatings) 5 (1995) 231-238.
M.J. Mouche et al., Thin Solid Films 262 (1995) 1-6.
R. Padiyath et al., Metallized Plastics 2 (1991) 113-120.
R. Padiyath et al., J. Appl. Phys. 73(5) 2326-2332 (1992).
J.K. Kim et al., Jan. 1999, Spie Conf. on Laser Applications in Microelectronic and Optoelectronic Manufacturing IV, San Jose, CA, USA (Proceedings SPIE-Int. Soc. Opt. Eng. 3618 (1999) 378-385.
Keller et al., Natura 162 (1948) 580-582.
D.A. Edwards, J. Chem. Soc. Dalton Trans. 1973, 2463-2468.
B. Begiun et al., J. Organomet. Chem. 208 (1981) C18-C20.
N. Marisch et al., J. Organomet. Chem 239 (1982) 429-437.
C. Bianchini et al., J. Organomet. Chem. 248 (1983) C13-C16.
G. Doyle et al., Organometallics 1 (1982) 1613-1618.
J. Chem. Soc., Trans., vol. 5, 2000, 753-761, XP008053157.
J. Inorg. Nucl. CHem., vol. 33, 1971, 1017-1024, XP 002347077.
Inorg. Chem., vol. 24, n. 6, 1985, 924-931, XP002347078.

* cited by examiner

*Primary Examiner*—Michael Cleveland
*Assistant Examiner*—Robert Vetere
(74) *Attorney, Agent, or Firm*—Connolly Bove Lodge & Hutz LLP

(57) ABSTRACT

Copper (I) formate complexes of general formula $L_nCu(HCOO) \cdot x$ COOH are decomposed in order to separate metallic copper, wherein x is a number from 0 to 10, n amounts to, 2, 3 or 4 and the n ligands L represent, independent of one another, one of the following ligands: a phosphane of formula $R^1R_2R_3P$; a phosphite of formula $(R^1O)(R^2O)(R^3O)P$; an isocyanide of formula $R^1$—NC; an alkene of general formula $R^1R^2C=CR^3R^4$; or an alkyne of general formula $R^1C\equiv CR^2$; wherein $R^1$, $R^2$, $R^3$ and $R^4$ represent, independent of one another, hydrogen, a linear or branched, optionally partly or fully fluorinated alkyl, aminoalkyl, alkyoxialkyl, hydroxialkyl, phosphinoalkyl or aryl radical having up to 20 carbon atoms, with the exception of triphenylphosphino-copper (I) formate and 1,1,1-tris(diphenylphosphinomethyl)ethane-copper (I) formate.

12 Claims, No Drawings

COPPER(I) FORMATE COMPLEXES

This application is the National Stage of International Application No. PCT/EP2004/014275 filed on Dec. 15, 2004; and this application claims priority of Application Ser. No. 103 60 046.9 filed in Germany on Dec. 18, 2003 under 35 U.S.C. §119; the entire contents of all are hereby incorporated by reference.

The present invention relates to copper(I) formate complexes. Owing to their property of decomposing with deposition of metallic copper, copper complexes are used in microelectronics, for example for depositing copper conductor tracks by deposition from the gas phase (chemical vapor deposition or CVD for short) or from a solution (spin-coating process). Such deposition processes can be used as an alternative to the conventional sputtering of copper (a process for physical vapor deposition, or PVD for short, in which no transformation of substances takes place) or to the application of copper seeds which lead to improved deposition and adhesion of copper layers subsequently applied by sputtering.

In The Chemistry of Metal CVD (Wiley-VCH Verlag GmbH & Co. KGaA, Weinheim, 1994, ISBN 3-527-29071-0), pages 239-302, T. T. Kodas and M. J. Hambden-Smith give an overview of known CVD processes for depositing copper and of conventional starting materials therefor. These are in particular copper(II) β-diketonate complexes, copper (I) β-diketonate complexes, copper(I) β-ketimide complexes, copper(I) β-diimide complexes, cyclopentadienylcopper(I) complexes and copper alkoxides. Owing to their stability, handling properties, availability and price, the diketonates are most frequently used, the greatest disadvantage thereof being their comparatively low copper yield, which is not more than 50% without the use of additional reducing agents. An alternative process for depositing copper, the spin-coating or spin-on-process, in which a solution of a nonvaporizable but decomposable copper compound or a copper dispersion is applied to a rotating substrate and is distributed by the rotation, and a uniform copper film is thus deposited, is described, for example, by D. K. Sohn, S. C. Park, S. W. Kang and B. T. Ahn in J. Electrochem. Soc. 144 (1977), 3592-3596.

Copper compounds or copper complexes with carboxylates or alkoxylates are generally known and can also be used for depositing metallic copper. F. A. Cotton, E. V. Dikarev and M. A. Terukhina, Inorg. Chem. 39 (2000), 6072-6079, describe copper(I) and copper(II) trifluoroacetate. Copper(I) trifluoroacetate is sublimable and would therefore be suitable in principle as a starting material for CVD. E. Iljina, A. Korjeva, N. Kuzmina, S. Troyanov, K. Dunaeva and L. Martynenko, Mater. Sci. Eng. B18 (1993), 234-236, disclose the preparation and the crystal structure of volatile copper(I) pivalate. S. A. Krupoder, V. S. Danilovich, A. O. Miller and G. G. Furin, J. Fluorine Chem. 73 (1995), 13-15, report the synthesis of and thermogravimetric investigations into volatile copper(II) bis(trifluoroacetate) complexes. M. E. Gross, J. Electrochem. Soc. 138 (8) (1991), 2422-2426, describes (partly) fluorinated copper(I) alkoxides and compares their volatility with (cyclopentadienyl)(triethylphosphino)copper (I) and carbonylcopper(I) tert-butoxide and the industrially commonest CVD starting material, bis(hexafluoroacetylacetonate)copper(II).

CN 12 40 689 A discloses the preparation of extremely fine copper powder by thermolysis of carboxylates. JP 06/184 749 describes the preparation of copper films by decomposition of tert-butoxycopper carbonyl. WO 01/13 426 A1 describes the use of copper(II) bis(2-ethylhexanoate), copper(II) (2-ethylhexanoate)isopropoxide and copper(II) (2-ethylhexanoat) methoxyethoxide for copper deposition. DE 41 38 722 A1 discloses a process for the vaporization of copper(II) tetramethylheptanedionate with the aid of benzyl alcohol. EP 976 847 A2 describes the production of a copper film from copper (II) bis(2-ethylhexanoate). DE 39 22 233 A1 describes the production of copper conductor tracks from copper(II)carboxylates by laser irradiation. WO 01/94 291 A1 discloses copper(II) complexes of the type $Cu(OCCF_3R^1CH_2NHR^2)_2$, where $R^1$ is hydrogen, $C_1$-$C_4$-alkyl or $C_1$-$C_4$-perfluroalkyl and $R^2$ is $C_1$-$C_6$-alkyl or $C_1$-$C_6$-alkene, which optionally may also be substituted by fluorine, alkoxy or alkylamino groups, and their use for depositing copper films. The prior German Patent Application with the application number DE 10325243.6 (filed on Jun. 3, 2003) describes the deposition of copper layers on substrates by bringing the substrate into contact with a compound of copper(II) formate and alkoxyalkylamines of the formula $R^1O(CH_2)_nCHR^2NH_2$, where $R^1$ is methyl or ethyl, $R^2$ is hydrogen or methyl and n is 1, 2, 3, or 4. K. Köhler, J. Eichhorn, F. Meyer and D. Vidovic, Organometallics 22 (2003), 4426-4432, report dicopper(I) oxalate complexes with alkyne or alkene ligands and the use thereof for copper deposition from solution by means of spin-coating or by spraying on a solution with decomposition (aerosol assisted CVD or AACVD for short).

Specifically, copper(II) formates and the deposition of metallic copper by decomposition of such compounds are also known. J.-K Kim, S.-K. Park and C. Lee, J., Korean Phys. Soc. 35(5) (1999), 426-430, describe the use of copper(II) formate tetrahydrate for producing microstructures by laser-induced copper deposition. M.-J. Mouche, J.-L. Mermet, C. Mathon and R. Cimard, Adv. Sci. Technol. (Adv. Inorg. Films and Coatings) 5 (1995), 231-238, as well as M.-J. Mouche, L. Mermet, M. Romand and M. Charbonnier, Thin Solid Films 262 (1995), 1-6, report the use of copper(II) formate hydrate as a starting material for CVD in a carrier gas. R. Padiyath, M. David and S. V. Babu, Metallized Plastics 2 (1991), 113-120, describe the production of copper films from copper(II) formate in a hydrogen plasma. R. Padiyath, J. Seth, S. V. Babu and L. J. Matienzo, J. Appl. Phys. 73(5) (1993), 2326-2332, report the deposition of copper on silicon and the formation of copper silicide by application of copper formate and reduction in a hydrogen plasma. J.-K. Kim and C. Lee reported in January 1999 at the SPIE Conference on Laser Applications in Microelectronic and Optoelectronic Manufacturing IV, San Jose, Calif., USA (cf. Proceedings SPIE-Int. Soc. Opt. Eng. 3618 (1999), 378-385) on the production of copper films from copper(II) formate by irradiation with an argon laser. Example 24 of EP 1 077 084 A2 discloses the deposition of copper on mordenite by thermal decomposition of copper formate. EP 368 231 A2 describes the deposition of copper by thermolysis of copper(II) formate on shaped resin articles. In the process of U.S. Pat. No. 5,141,602 A, copper is deposited by decomposition of copper(II) formate by means of laser irradiation, and in the process of JP 11/193 461 A, copper is once again deposited by thermal decomposition.

A. Keller and F. Körösy, Nature 162 (1948), 580-582, report the decomposition of copper(I) formate, which they describe as CuHCOO and prepare by careful decomposition of copper(II) formate, to copper, carbon dioxide and hydrogen on heating to 105° C. D. A. Edwards and R. Richards, J. Chem. Soc. Dalton Trans. (1973), 2463-2468, describe the synthesis of copper(I) formate by reacting copper(II) formate with metallic copper in formic acid. Copper(I) formates are otherwise known in particular in the form of ligand-stabilized complexes, usually of the type $L_nCu(HCOO)$, where $L_n$ is either an at least bidentate ligand L (n=1) or (n=2, 3 or 4) 2, 3 or 4 at least monodentate ligands L. B. Beguin, B. Denise and R. P. A. Sneeden, J. Organomet. Chem. 208 (1981), C18-C20, describe the copper(I) formate complex $(PPh_3)_2Cu(HCOO)$, which is prepared from $[HCuPPh_3]_6$, $PPh_3$ and $CO_2$. N. Marisch, A. Camus and G. Nardin, J. Organomet. Chem. 239 (1982), 429-437, report the crystal structure of $(PPh_3)_2Cu(HCOO)$ and its pyrolysis at 200° C., whereby it decomposes substantially into copper, $CO_2$ and $PPh_3$. C. Bianchini, C. A. Ghilardi, A. Meli, S. Midollini and A. Orlandini, J. Organomet. Chem. 248 (1983), C13-C16, describe the synthesis and the structure of (triphos)Cu(HCOO), where triphos=1,1,1-tris(diphenylphosphinomethyl)ethane. This complex is prepared by reacting $(triphos)Cu(BH)_4$ with $CO_2$. G. Doyle, K. A. Eriksen, M. Modrick and G. Ansell, Organometallics 1 (1982), 1613-1618, report the synthesis of the complex salt $[(tmeda)Cu_2(CO)(HCOO)]^+[BPh_4]^-$ (tmeda=N,N,N',N'-tetramethylethylendiamine, Ph=phenyl) from tmeda, copper(I) oxide, carbon monoxide, formic acid and sodium tetraphenylboranate. All these copper(I) formates are compounds prepared in very small amounts for purely scientific purposes, and, simply because of the inconvenient preparation, their decomposition for the purpose of copper deposition was never a matter of discussion for economic reasons.

There continues to be a need for copper compounds which are more suitable for use as a starting material for depositing metallic copper by means of CVD than known compounds. Substantial requirements are a high copper content, easy accessibility, low costs, high stability during handling and storage, but easy decomposition during the coating of the substrate, although, apart from copper, no nonvolatile impurities should form since they would be deposited on the substrate.

It is an object of the present invention to provide such copper compounds and processes for their preparation and for the deposition of copper by their decomposition.

We have found that this object is achieved by copper(I) formate complexes of the formula $L_nCu(HCOO)\cdot x\ HCOOH$, where x is from 0 to 10, n is 1, 2, 3 or 4 and the n ligands L, independently of one another, are each one of the following ligands:
  a phosphane of the formula $R^1R^2R^3P$;
  a phosphite of the formula $(R^1O)(R^2O)(R^3O)P$;
  an isocyanide of the formula $R^1$—NC;
  an alkene of the formula $R^1R^2C=CR^3R^4$; or
  an alkyne of the formula $R^1C\equiv CR^2$;
  where $R^1$, $R^2$, $R^3$ and $R^4$, independently of one another, are hydrogen, a linear or branched, optionally partly or completely fluorinated alkyl, aminoalkyl, alkoxyalkyl, hydroxyalkyl, phosphinoalkyl or aryl radical of one to 20 carbon atoms;
  with the exception of triphenylphosphine and 1,1,1-tris(diphenylphosphinomethyl)ethane.

We have also found processes for the preparation of these novel copper(I) formate complexes, a process for the preparation of the starting material copper(I) formate for one of these processes, and processes for depositing copper by decomposing the novel copper(I) formate complexes.

The novel copper(I) formate complexes are of the formula $L_nCu(HCOO)\cdot x\ HCOOH$. Such copper(I) formate complexes may also be present as polynuclear complexes, i.e. formally as oligomers $[L_nCu(HCOO)\cdot x\ HCOOH]_m$, where m is an integer and is at least 2. Whether the novel complexes undergo an addition reaction to give polynuclear complexes depends substantially on the ligand L.

The number x in the above formula is a number which may be equal to zero but in general is typically at least 0.1, preferably at least 0.5, particularly preferably at least 1, and in general not more than 10, preferably not more than 5, particularly preferably not more than 2. Very particularly preferably, x is 1.

In the formula, n is 1, 2, 3 or 4. Preferably, n is 2 or 3.

L is one of the following ligands which, when n is greater than 1, are chosen independently of one another:
  a phosphane of the formula $R^1R^2R^3P$;
  a phosphite of the formula $(R^1O)(R^2O)(R^3O)P$;
  an isocyanide of the formula $R^1$—NC;
  an alkene of the formula $R^1R^2C=CR^3R^4$; or
  an alkyne of the formula $R^1C\equiv CR^2$;

where $R^1$, $R^2$, $R^3$ and $R^4$, in each case independently of one another, are:
  hydrogen or
  a linear or branched, optionally partly or completely fluorinated alkyl, aminoalkyl, alkoxyalkyl, hydroxyalkyl, phosphinoalkyl or aryl radical of one to 20 carbon atoms.

Examples of such linear or branched alkyl radicals are the methyl, ethyl, n-propyl, isopropyl, n-butyl, sec-butyl, isobutyl, tert-butyl and 2-ethylhexyl radicals, the isomeric pentyl, hexyl, heptyl, octyl, nonyl, decyl, undecyl or dodecyl radicals and the cyclic alkyl radicals, such as cyclopropyl, cyclobutyl, cyclopentyl, cyclohexyl, cycloheptyl, cyclooctyl and bicyclononyl radicals, which may also carry alkyl substituents. Instead of hydrogen, the carbon atoms may also carry other substituents, for example halogen substituents, in particular fluorine. Two or more of the radicals may also form a closed ring system which may also be unsaturated. An example of such a ligand L is cyclopentadienyl, which is formally an olefin $R^1R^2C=CR^3R^4$.

Examples of such aminoalkyl, alkoxyalkyl, hydroxyalkyl and phosphinoalkyl radicals are said alkyl radicals substituted by one or more amino groups, alkylamino groups, alkoxy groups, hydroxyl groups, phosphinoalkyl and/or alkylphosphinoalkyl radicals.

Examples of such aryl radicals are phenyl and naphthyl radicals, which may also be substituted by said alkyl, aminoalkyl, alkoxyalkyl, hydroxyalkyl and phosphinoalkyl radicals.

The ligands L, independently of one another, are preferably each a phosphane of the formula $R^1R^2R^3P$, a phosphite of the formula $(R^1O)(R^2O)(R^3O)P$ or an isocyanide of the formula $R^1$—NC.

Preferred radicals $R^n$ (n=1, 2 or 3) are the methyl, ethyl, isopropyl, n-butyl, tert-butyl, cyclopentyl or cyclohexyl radicals.

Particularly preferred ligands are the trialkylphosphine radicals, such as trimethylphosphine, triethylphosphine, triisopropylphosphine, tri-n-butylphosphine, triisobutylphosphine or tricyclopentylphosphine, the trialkylphosphite radicals, such as trimethoxyphosphine, triethoxyphosphine, triisopropoxyphosphine and tri(2,2,2-trifluorethoxi)phosphine, and the alkyl isocyanides, such as isopropyl isocyanide, n-butyl isocyanide, tert-butyl isocyanide and cyclohexyl isocyanide. Tri-n-butylphosphine is a very particularly preferred ligand.

Triphenylphosphine and 1,1,1-tris(diphenylphosphinomethyl)ethane are accepted from the formula of the novel copper(I) formate complexes.

Three processes for the preparation of the novel copper(I) formate complexes were found.

The first such novel process starts from copper(I) formate. Processes for the preparation of copper(I) formate are known. Copper(I) formate is reacted in a dry, inert solvent by adding the desired stoichiometric amount of the ligand or ligands L to the novel copper(I) formate complexes. All inert solvents are suitable as the inert solvent. Aprotic polar solvents are particularly suitable. Examples of suitable solvents are ethers, such as diethyl ether, dipropyl ether, dibutyl ether, tetrahydrofuran, tert-butyl methyl ether or tert-butyl ethyl ether, and halogenated, in particular chlorinated, alkane solvents, such as methylene chloride and chloroform. Tetrahydrofuran and methylene chloride are preferably used. For carrying out the reaction, the copper(I) formate is conveniently initially taken in solution or as a suspension, and a solution of n mole equivalents of the ligand or ligands is added with stirring. The copper(I) formate complex is then obtained, for example by crystallization optionally also by removal of the solvent, for example by evaporation under reduced pressure or by crystallization after partial removal of the solvent. Complexes which are prepared by this process generally contain no formic acid (x=0), but, if desired, a corresponding amount of formic acid may be added during the synthesis.

In the context of the present invention, a process for the preparation of the novel copper(I) formate complexes has also been found, in which the not very stable ligand-free copper(I) formate must not be isolated and handled as a substance. In this process, anhydrous copper(II) formate is reacted with metallic copper (usually used in stoichiometric excess, for example as wire, dispersion, granules or foil) and one mole equivalent of formic acid optionally in an inert solvent. All inert solvents are suitable as the inert solvent, in particular aprotic polar solvents. Examples of suitable solvents are ethers, such as diethyl ether, dipropyl ether, dibutyl ether, tetrahydrofuran, tert-butyl methyl ether or tert-butyl ethyl ether, halogenated, in particular chlorinated, alkane solvents, such as methylene chloride and chloroform, and acetonitrile. Acetonitrile is preferably used. The reaction mixture is allowed to react until the reaction is complete, which is generally the case after a reaction time of at least one hour, preferably at least 2, particularly preferably at least 4, hours and in general after not more than 48, preferably not more than 36, particularly preferably not more than 30, hours. Thereafter, the desired ligand L is added in the desired stoichiometric amount and the reaction mixture is allowed to react further until the end of complex formation. In general, the complex formation is complete after a reaction time of at least five, preferably at least 10, particularly preferably at least 30, minutes and in general after not more than 6, preferably not more than 4, particularly preferably not more than 2, hours. The solid (substantially unreacted copper) is then separated off, the solvent is removed and the product is thus obtained. In this form of the preparation of the novel copper(I) formate complexes, the complex prepared contains formic acid, the amount of which is established according to the chosen ligand L and its amount n.

Furthermore, some of the novel copper(I) formate complexes $L_nC(HCOO)$, i.e. those whose halide analogs, in particular chloride analogs $L_nCuX$, where X is halide, e.g. Cl, are known, can be prepared by reacting these halide complexes with formic acid and a base. For this purpose, the desired stoichiometric amount of formic acid is added to the halide complex in a solvent. The stoichiometric amount of formic acid is at least as much as the amount of the halide complex. If a novel copper(I) formate complex containing formic acid (i.e. where x>0) is to be prepared, the stoichiometric amount of formic acid is appropriately chosen. Suitable inert solvents are in particular all those inert solvents in which either the byproduct formed from base and halide is better soluble than the copper(I) formate complex, or vice versa. Aprotic polar solvents are particularly suitable. Examples of suitable solvents are ethers, such as diethyl ether, dipropyl ether, dibutyl ether, tetrahydrofuran, tert-butyl methyl ether or tert-butyl ethyl ether, and halogenated, in particular chlorinated, alkane solvents, such as methylene chloride and chloroform. An ether, in particular tert-butyl methyl ether, is preferably used; in these cases, in general the copper(I) formate complex has better solubility than the byproduct. In general, the exchange of the halide with formate is complete after a reaction time of at least five, preferably at least 10, particularly preferably at least 30, minutes and in general after not more than 6, preferably not more than 4, particularly preferably not more than 2, hours. The halide is then precipitated by adding a base. Particularly suitable bases are primary, secondary or tertiary amines, for example and preferably triethylamine. The reaction mixture is allowed to react further after addition of the base, in general for a reaction time of at least one hour, preferably at least 2, particularly preferably at least 4, hours and in general not more than 12, preferably not more than 8, particularly preferably not more than 6, hours. Product and byproduct are then separated. If the product is better soluble in the solvent used than the byproduct, the latter is filtered off and the solvent is then removed. The dried residue can be taken up in an extracting agent for further purification and said extracting agent can then once again be freed from the solid. Suitable extracting agents are all solvents in which the novel copper(I) formate complex is soluble but not the reaction product of hydrogen halide with the base, which reaction product is formed as a byproduct. Aprotic nonpolar or slightly polar solvents are particularly suitable. Examples of suitable solvents are alkanes or aromatic hydrocarbons, such as pentane, hexane, gasoline, petroleum, benzene or toluene. Hexane is preferably used. The extracting agent is removed after the removal of solids, and the product is thus obtained. If, on the other hand, the product is more poorly soluble in the chosen solvent than the byproduct, it is filtered off, if necessary after evaporating down the solvent.

In the same way, ligand-free copper(I) formate can also be obtained from copper(I) halide, in particular copper(I) chloride, by reaction thereof with formic acid and a base.

The reaction temperature during these reactions and also the temperature used during the removal of the solvent should be sufficiently high for the reaction or solvent removal to take place at a satisfactory rate, but not so high that the copper(I) formate begins to decompose. In general, a temperature of at least $-20°$ C., preferably at least $0°$ C., particularly preferably at least $10°$ C., and in general not more than $80°$ C., preferably not more than $60°$ C., particularly preferably not more than $40°$ C., is established. In general, room temperature, i.e. in the range from 20 to $25°$ C., can be employed without problems, and the solvent removal should, if appropriate, be carried out under reduced pressure in order to achieve satisfactory rates.

In all cases, the syntheses are preferably carried out in the absence of air, in particular oxygen. Conventional inert gas techniques are employed. Suitable inert gases are conventional inert gases, in particular nitrogen or argon. It is also preferable, as far as possible, to work in an anhydrous environment.

The novel copper(I) formate complexes are applied to the substrates by known methods, such as CVD, AACVD or spin-coating and are thermally decomposed thereby or thereafter with copper deposition. Cohesive copper films form. In AACVD and in spin-coating, the novel copper(I) formate complexes are preferably used in the form of a solution in an inert solvent. Suitable inert solvents are all solvents in which the novel copper(I) formate complex used is sufficiently soluble and which are also inert to the substrate under the conditions employed. They should also be very readily vaporizable and hence easily removable. Examples of suitable solvents are polar or nonpolar aprotic solvents, for example ethers, such as diethyl ether, dipropyl ether, dibutyl ether, tetrahydrofuran, tert-butyl methyl ether or tert-butyl ethyl ether, and halogenated, in particular chlorinated, alkane solvents, such as methylene chloride and chloroform, alkanes and aromatic hydrocarbons, such as pentane, hexane, gasoline, petroleum, benzene or toluene. The concentration of formate complex in the solution is chosen so that the viscosity of the solution permits easy handling and so that uniform copper films form. In general, a solution which contains at least 0.5, preferably at least 3, particularly preferably at least 5, and in general not more than 40, preferably not more than 30, particularly preferably not more than 20% by weight of the copper(I) formate complex is used.

For application by means of AACVD, the complex or a solution of the complex is usually sprayed onto the heated substrate or the sprayed substrate is then heated to decomposition temperature. For application by means of spin-coating, the complex or a solution of the complex is usually applied to the rotating substrate so that a uniform layer of the liquid is produced by the centrifugal force. The substrate is heated to the decomposition temperature during the application or subsequently.

For the deposition of a copper layer on a substrate by decomposition of a novel copper(I) formate complex, the substrate is heated to a temperature above the decomposition temperature of the complex during the application of the complex or immediately thereafter. In general, heating is effected to a temperature of at least 80° C., preferably at least 100° C., particularly preferably at least 105° C., and in general not more than 300° C., preferably not more than 280° C., particularly preferably not more than 250° C.

EXAMPLES

Example 1

Preparation of Copper(I) Formate

A solution of 0.92 g of formic acid (20 mmol) in 20 ml of methylene chloride was added to a suspension of 1.98 g of copper(I) chloride CuCl (20 mmol) in 40 ml of dry methylene chloride with stirring under nitrogen in the course of 5 minutes at room temperature. After 10 minutes, 2.02 g of anhydrous triethylamine (20 mmol) were added. The mixture was stirred for a further 4 hours, after which the resulting pale green precipitate of copper(I) formate was filtered off over a reverse frit and washed with 20 ml of methylene chloride. The yield was 95 mol %.

Example 2

Preparation of the Novel Complexes from Copper(I) Formate and Ligand

A solution of n equivalents of the ligand (1 equivalent per 8.3 mmol) in 20 ml of dry methylene chloride or tetrahydrofuran was slowly added under nitrogen to a stirred suspension of 8.3 mmol of copper(I) formate in 20 ml of methylene chloride or THF. After about one hour in each case, the copper(I) formate had completely dissolved. After the solvent had been stripped off under reduced pressure, the copper(I) formate complexes were obtained as colorless oils or solids.

Example 3

Preparation of the Novel Complexes from Copper(I) Chloride Complexes 4.6 g (0.1 mol) of formic acid were added to a solution of 0.1 mol of a copper(I) chloride of the formula $L_nCuCl$ in 200 ml of methyl tert-butyl ether at 0° C. with stirring, and stirring was continued for a further hour. Thereafter, 10.1 g (0.1 mol) of anhydrous triethylamine were added and stirring was effected for 5 hours at room temperature. Thereafter, the solvent was removed at 40° C. under reduced pressure and the solid residue was extracted with twice 100 ml of hexane. The combined extracts were freed from the hexane at 40° C. under reduced pressure and the product thus obtained.

Example 4

Preparation of a Novel Complex Without Isolation of Copper(I) Formate Formed as an Intermediate 1.53 g of anhydrous copper(II) formate $Cu(HCOO)_2$ (10 mmol), 1.6 g of 98% strength formic acid and 2.7 g of copper foil were stirred for 24 hours under nitrogen in 60 ml of anhydrous acetonitrile. A colorless solution formed above unconverted solid copper. 6.65 g of triethoxyphosphane (40 mmol) were then added dropwise. The reaction mixture was stirred for a further hour, and the copper foil was then filtered off. The product $[(H_3CH_2CO)_3P]_2Cu(HCOO)\cdot x$ HCOOH was obtained as a colorless liquid by evaporating down the filtrate.

The copper(I) formate complexes $L_nCu(HCOO)\cdot x$ HCOOH prepared as examples by these methods are listed in the table below together with the chemical shifts δ of the phosphine ligands in $^{31}$P-NMR and those of the formate carbons and formate protons in $^{13}$C-NMR and $^1$H-NMR

TABLE

| Ligand L | n | Prepared acc. to example | State of aggregation | $^{31}$P-NMR δ [ppm] | $^{13}$C-NMR δ [ppm] | $^1$H-NMR δ [ppm] |
| --- | --- | --- | --- | --- | --- | --- |
| $(H_3C)_3P$ | 2 | 2, 3 | liquid | −45.7 | 166.7 | 8.4 |
| $(H_3CH_2C)_3P$ | 2 | 2, 3 | liquid | −12.2 | 165.4 | 8.3 |
|  | 3 | 2, 3 | liquid | −14.4 | 164.3 | 8.5 |

TABLE-continued

| Ligand L | n | Prepared acc. to example | State of aggregation | $^{31}$P-NMR δ [ppm] | $^{13}$C-NMR δ [ppm] | $^{1}$H-NMR δ [ppm] |
|---|---|---|---|---|---|---|
| [(H$_3$C)$_2$HC]$_3$P | 2 | 2, 3 | liquid | 22.1 | 167.2 | 8.3 |
| (H$_3$CH$_2$CH$_2$CH$_2$C)$_3$P | 2 | 2, 3 | liquid | −25 | 165.7 | 8.4 |
|  | 3 | 2, 3 | solid | −22 | 166.8 | 8.5 |
| [(H$_3$C)$_2$HCH$_2$C]$_3$P | 2 | 2, 3 | liquid | −28.5 | 164.1 | 8.2 |
| (C$_5$H$_9$)$_3$P | 2 | 2, 3 | solid | 8.3 | 164.7 | 8.2 |
|  | 3 | 2, 3 | solid | 9.6 | 165.2 | 8.3 |
| (H$_3$CO)$_3$P | 2 | 2, 3 | liquid | 126.5 | 167.3 | 8.6 |
|  | 3 | 2, 3 | liquid | −126.9 | 167 | 8.6 |
| (H$_3$CH$_2$CO)$_3$P | 2 | 2, 3, 4 | liquid | 122.9 | 166.6 | 8.4 |
|  | 3 | 2, 3 | solid | 117.9 | 165.8 | 8.5 |
| [(H$_3$C)$_2$HCO]$_3$P | 2 | 2, 3 | solid | 117 | 169 | 8.2 |
|  | 3 | 2, 3 | solid | 121.6 | 168.5 | 8.3 |
| (F$_3$CH$_2$CO)$_3$P | 2 | 2, 3 | liquid | 119.8 | 159.5 | 8.1 |
| (C$_6$H$_5$)$_3$P | 2 | 2, 3 | solid | −3.3 | 169.2 | 8.5 |
| (H$_3$C)$_2$HC—NC | 2 | 2 | solid | — | 140.5 | 8.2 |
| H$_3$CH$_2$CH$_2$C—NC | 2 | 2 | solid | — | 140.5 | 8.2 |
| (H$_3$C)$_3$C—NC | 2 | 2 | solid | — | 129 | 8.5 |
| H$_{11}$C$_6$—NC | 2 | 2 | liquid | — | 152.4 | 8.6 |

Example 5

Thermogravimetric Investigation of [(H$_3$CH$_2$CO)$_3$P]$_2$Cu(HCOO)

A thermogravimetric investigation of the complex [(H$_3$CH$_2$CO)$_3$P]$_2$Cu(HCOO) confirmed, that, as calculated, it consisted of 14.4% by weight of copper and of 85.6% by weight of organic components and showed that it lost exactly 85.6% of its original weight on heating to temperatures of at least 150° C. This confirms that the complex decomposes to copper and otherwise, under these conditions, exclusively other, gaseous decomposition products.

Example 6

Deposition of a Copper Film

A 10% strength solution of [(H$_3$CH$_2$CO)$_3$P]$_2$Cu(HCOO) in methylene chloride was sprayed into a glass flask heated to 200° C. A copper film formed on the inside of the flask.

Example 7

Deposition of a Copper Film

The inner surface of a glass flask was wet with a 10% strength solution of [(H$_3$CH$_2$CO)$_3$P]$_2$Cu(HCOO) in methylene chloride. By careful evaporation of the solvent, a thin film of the formate complex was produced on the inner surface of the flask. The flask was then heated to 200° C. A copper film formed on the inside of the flask.

We claim:

1. A copper(I) formate complex of the formula L$_n$Cu(HCOO).x HCOOH, where x is from 0 to 10, n is 1, 2, 3 or 4 and the n ligands L, independently of one another, are each one of the following ligands:
   a phosphane of the formula R$^1$R$^2$R$^3$P;
   a phosphite of the formula (R$^1$O)(R$^2$O)(R$^3$O)P;
   an isocyanide of the formula R$^1$—NC;
   an alkene of the formula R$^1$R$^2$C=CR$^3$R$^4$; or
   an alkyne of the formula R$^1$C≡CR$^2$;
   where R$^1$, R$^2$, R$^3$ and R$^4$, independently of one another, are hydrogen, a linear or branched, optionally partly or completely fluorinated alkyl, aminoalkyl, alkoxyalkyl, hydroxyalkyl, phosphinoalkyl or aryl radical of one to 20 carbon atoms;

with the exception of triphenylphosphinocopper(I) formate and 1,1,1-tris(diphenyl-phosphinomethyl) ethanecopper(I) formate.

2. The copper(I) formate complex according to claim 1, wherein n is 2 or 3.

3. The copper(I) formate complex according to claim 1, wherein L is selected from the group consisting of trimethylphosphine, triethyiphosphine, triisopropylphosphine, tri-n-butylphosphine, triisobutylphosphine, tricyclopentylphosphine, trimethoxyphosphine, triethoxyphosphine, triisopropoxyphosphine,tri(2,2,2-trifluoroethoxy)phosphine, isopropyl isocyanide, n-butyl isocyanide, tert-butyl isocyanide and cyclohexyl isocyanide.

4. The copper(I) formate complex according to claim 3, wherein L is tri-n-butylphosphine.

5. The copper(I) formate complex according to claim 4, wherein x is 1.

6. A process for the preparation of a copper(I) formate complex defined in claim 1 by reacting copper(I) formate with ligand L and optionally formic acid.

7. The process according to claim 6, wherein the copper(I) formate is obtained in a first step from copper(II) formate, metallic copper and formic acid and is not isolated before addition of the ligand L.

8. A process for the preparation of a copper(I) formate complex defined in claim 1 by reacting a copper(I) halide complex of the formula L$_n$Cu(I)X, where X is a halide and L and n have the meanings defined in claim 1, with formic acid and then with a base.

9. A process for depositing metallic copper on a substrate by application of a copper(I) formate complex defined in claim 1 to the substrate and thermal decomposition of the copper(I) formate complex at a temperature of at least 80° C.

10. The process according to claim 9, wherein the copper(I) formate complex is deposited from the gas phase and simultaneously decomposed.

11. The A process according to claim 9, wherein the substrate is sprayed with a solution of the copper(I) formate complex and the latter is simultaneously or subsequently decomposed.

12. The process according to claim 9, wherein a solution of the copper(I) formate complex is applied to a rotating substrate and the copper(I) formate complex is simultaneously or subsequently decomposed.

* * * * *